US011957803B2

(12) United States Patent
Lee et al.

(10) Patent No.: US 11,957,803 B2
(45) Date of Patent: Apr. 16, 2024

(54) ULTRAVIOLET APPARATUS FOR FOOD DISINFECTION

(71) Applicants: Jiyoon Lee, Seoul (KR); Sungyeon Kim, Seoul (KR); Taeyeon Kim, Seoul (KR)

(72) Inventors: Jiyoon Lee, Seoul (KR); Sungyeon Kim, Seoul (KR); Taeyeon Kim, Seoul (KR)

(73) Assignees: Jiyoon Lee, Seoul (KR); Sungyeon Kim, Seoul (KR); Taeyeon Kim, Seoul (KR)

( * ) Notice: Subject to any disclaimer, the term of this patent is extended or adjusted under 35 U.S.C. 154(b) by 442 days.

(21) Appl. No.: 17/244,935

(22) Filed: Apr. 29, 2021

(65) Prior Publication Data

US 2021/0338865 A1 Nov. 4, 2021

Related U.S. Application Data

(60) Provisional application No. 63/019,073, filed on May 1, 2020.

(51) Int. Cl.
*A61L 2/10* (2006.01)
*A23L 3/00* (2006.01)
*A23L 3/28* (2006.01)
*B65B 55/08* (2006.01)

(52) U.S. Cl.
CPC ............... *A61L 2/10* (2013.01); *A23L 3/001* (2013.01); *A23L 3/003* (2013.01); *A23L 3/28* (2013.01); *B65B 55/08* (2013.01); *A23V 2002/00* (2013.01); *A61L 2202/11* (2013.01); *A61L 2202/14* (2013.01)

(58) Field of Classification Search
CPC .... A61L 2/10; A61L 2202/11; A61L 2202/14; A23L 3/001; A23L 3/003; A23L 3/28; B65B 55/08; A23V 2002/00
USPC ........................... 250/453.11, 454.11, 455.11
See application file for complete search history.

(56) References Cited

U.S. PATENT DOCUMENTS

2015/0343103 A1* 12/2015 Grajcar ..................... A61L 2/00
422/24
2018/0236114 A1* 8/2018 Davis ........................ A61L 2/24

* cited by examiner

*Primary Examiner* — Nicole M Ippolito
(74) *Attorney, Agent, or Firm* — H.C. Park & Associates, PLC; Jae Hoon Kim (57) ABSTRACT

A disinfecting apparatus including a housing to accommodate at least one tray therein, the housing having a first side and a second side, an ultraviolet (UV) light source disposed in the housing and configured to emit UV light towards the tray, and a plurality of doors including a first door and a second door disposed on the first side and the second side of the housing, respectively, in which the first door and the second door are configured to be opened in a direction away from the housing.

20 Claims, 7 Drawing Sheets

ULTRAVIOLET APPARATUS FOR FOOD DISINFECTION

CROSS-REFERENCE TO RELATED APPLICATION

This application claims priority from and the benefit of the U.S. Provisional Application No. 63/019,073, filed on May 1, 2020, which is hereby incorporated by reference for all purposes as if fully set forth herein.

BACKGROUND

Field

Exemplary embodiments relate to an apparatus for disinfecting food and/or food container, and more particularly, to an apparatus for disinfecting food and/or food container using ultraviolet light.

Description of the Related Art

Foods and containers for foods (or packaging) are contacted by many people before they are finally consumed by a consumer. For example, chefs, servers, and even cashiers may touch the food or the container during the preparation, serving, and packaging of the food. As such, before the foods are finally delivered to the hands of a consumer, there are risks of the foods and the container being exposed to virus or other harmful bacteria from direct human contact or indirect human contact, such as via aerosol.

Most viruses are known to be eliminated when exposed to ultraviolet (UV) light or near ultraviolet light in a wavelength range of about 160 nm to about 400 nm for a predetermined amount of time. Ultraviolet light is generally classified into UV-A, UV-B, and UV-C according to wavelength ranges. For example, UV-C has a wavelength range from about 200 nm to about 280 nm, UV-B has a wavelength range from about 280 nm to about 315 nm, and UV-A has a wavelength range from about 315 nm to about 400 nm. UV-C light is known to be germicidal, which deactivates the DNA of bacteria, viruses, and other pathogens and destroy their ability to multiply and cause disease, thereby causing sterilization of the microorganisms. While susceptibility to UV light varies, exposure to UV energy for about 20 to about 34 milliwatt-seconds/cm$^2$ is generally accepted for deactivating approximately 99 percent of the pathogens.

A conventional disinfecting apparatus may utilize UV light source for sterilization of food. However, conventional disinfecting apparatuses have an access door placed only at one surface of the apparatus. In this case, when a consumer does not have an access to the disinfecting apparatus, the server who delivers the food to the customer from the disinfecting apparatus would have to touch the food or the container after sterilization is completed. Even when a consumer has an access to the disinfecting apparatus, in this case, numbers of consumers and servers, as well as the chefs who place the food in the disinfecting apparatus, would be using the same door to access internals of the UV disinfecting apparatus.

Recently discovered viruses, such as COVID 19, are known to be contagious between people even by a mere contact to the same object. As such, people sharing the object, such as the access door of a disinfecting apparatus, would impose the risks of contaminating the food or the container with virus or germs.

The above information disclosed in this Background section is only for understanding of the background of the inventive concepts, and, therefore, it may contain information that does not constitute prior art.

SUMMARY

The inventive concepts are directed to an ultraviolet (UV) apparatus capable of eliminating virus or pathogens in the food and/or the container by providing multiple accesses to the UV apparatus so as to avoid the food and/or the container that have been sterilized from being contacted by people other than the consumer.

Additional features of the inventive concepts will be set forth in the description which follows, and in part will be apparent from the description, or may be learned by practice of the inventive concepts.

According to an exemplary embodiment, a disinfecting apparatus includes a housing to accommodate at least one tray therein, the housing having a first side and a second side, an ultraviolet (UV) light source disposed in the housing and configured to emit UV light towards the tray, and a plurality of doors including a first door and a second door disposed on the first side and the second side of the housing, respectively, wherein the first door and the second door are configured to be opened in a direction away from the housing.

The first side and the second side may be opposite to each other.

The first side and the second side may be adjacent to each other.

The disinfecting apparatus may further include a first access button to open at least one of the first door and the second door.

The first access button may be disposed in the first side of the housing.

The first access button may be disposed remotely from the housing.

The disinfecting apparatus may further include a second access button to open the other one of the first door and the second door.

The second access button may be disposed at a lower elevation that the of the first access button.

The size and the number of the first door may be different from those of the second door.

The disinfecting apparatus may further include a processor to sequentially operate the first door, the UV light source, and the second door.

The disinfecting apparatus may further include a locking unit disposed in the housing, in which the processor may cause the locking unit to keep the first and second doors from opening while the UV light source emits UV light.

The UV light source may be configured to emit light having a wavelength in a range of about 200 nm to about 280 nm.

The UV light source may be configured to emit UV light towards the tray less than about 30 seconds.

The UV light source may be configured to emit UV light towards the tray for about 10 to about 20 seconds at about 0.1 joules/cm$^2$.

The tray may be configured to extend outwardly from the housing via the second door once the UV light emission has been completed.

The ultraviolet (UV) light source may include a first UV lighting unit and a second UV lighting unit configured to emit light having different wavelengths.

The disinfecting apparatus may further include a lighting unit configured to illuminate the interior of the housing.

The lighting unit may be configured to emit light having a first color when the first door is opened, and may be configured to emit light having a second color different from the first color when the second door is opened.

The disinfecting apparatus may further include a reflective film disposed in the housing.

The disinfecting apparatus may further include a rail disposed inside the housing, and a mount on which the UV light source is disposed and coupled to the rail, in which the mount may be configured to slide along the rail within the housing while emitting UV light towards the tray.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIGS. 1, 2, 3, and 4 are schematic views of an ultraviolet (UV) apparatus according to exemplary embodiments.

Figure 1:
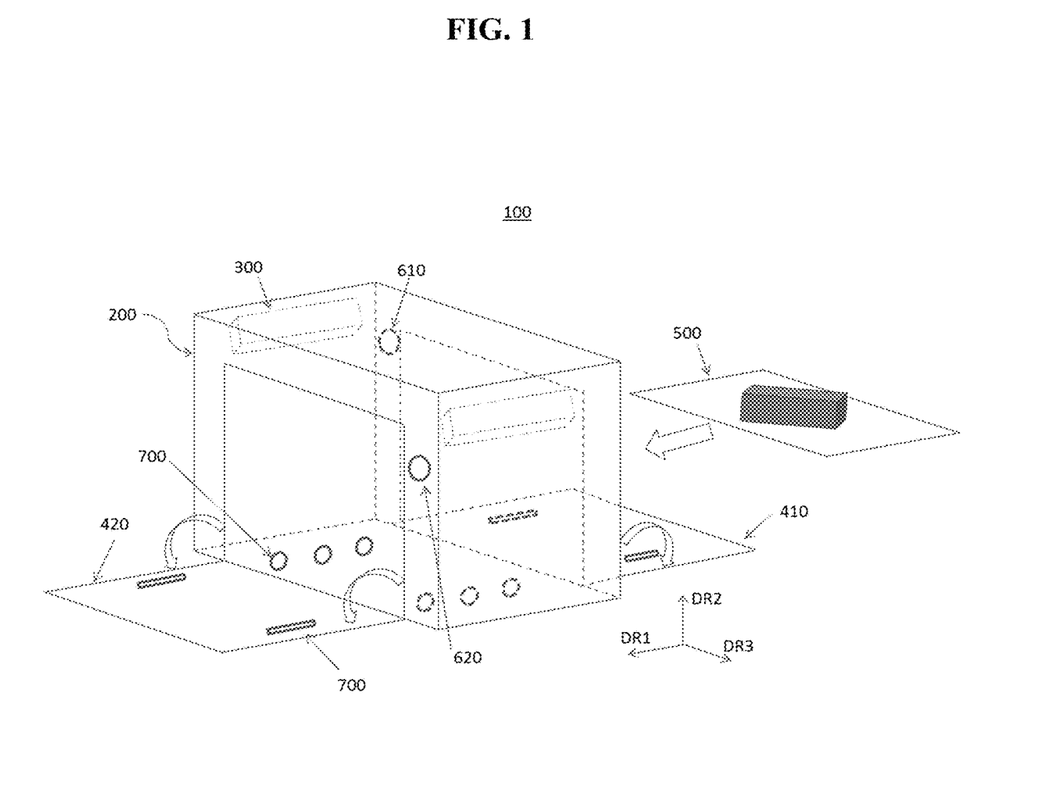
FIGS. 1 and 2 are schematic views of a UV apparatus according to an exemplary embodiment.
Figure 2:
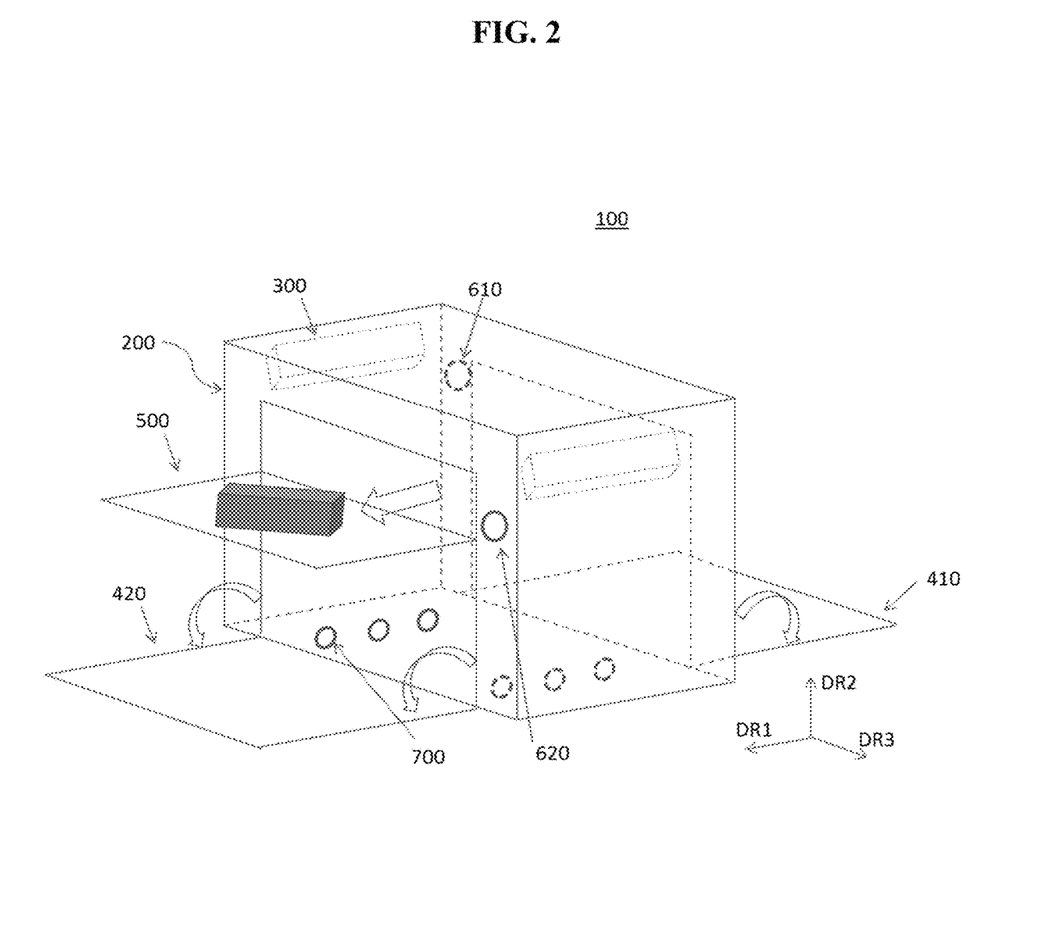

Referring to FIG. 1, the UV apparatus 100 according to an exemplary embodiment includes a housing 200, at least one UV light source 300, and a plurality of doors 400. The housing 200 may accommodate a tray 500, on which the food and/or the container may be placed for sterilization and/or disinfection. While FIG. 1 exemplarily shows one tray 500, the inventive concepts are not limited to a particular number of the trays 500 that may be accommodated in the housing 200. For example, in some exemplary embodiments, the housing 200 may accommodate at least two or more trays 500 therein. The tray 500 may be fixed into the housing 200, may extend outwardly from the housing 200 while having one or more ends coupled to the housing 200 as shown in FIG. 2, or may be detachably coupled to the housing 200. The tray 500 may provide a surface on which the foods and/or the container may be placed, and the shape or the materials thereof are not particularly limited. As used herein, the food may encompass raw, fresh, frozen, cooked, and semi-cooked foods, as well as beverages. Container as used herein may encompass any medium in which the food may be contained or packaged, such as to-go box or plates, and may also encompass utensil. The chef as used herein may include any person touching the food or the container before sterilization, and the server may encompass any person accessing the food after sterilization. As used herein, the terms sterilization and disinfection may be used interchangeably, and may refer that pathogen, bacteria, virus, germs, and the like are killed or cause less harm to human once being exposed to UV light for a predetermined amount of time. In addition, while the UV apparatus 100 in FIG. 1 is exemplarily shown as having substantially a rectangular shape, the inventive concepts are not limited to a particular shape of the UV apparatus 100. For example, in some exemplary embodiments, the UV apparatus 100 may have a polygonal shape, a circular shape, or a semi-circular shape. The housing 200 may have a structure that prevents UV light from the UV light source 300 from being directly irradiated towards the user.

The UV light source 300 may emit UV light having a wavelength in a range of about 160 nm to about 400 nm, more particularly, in a range of about 200 nm to about 280 nm, which is capable of killing viruses and germs therein. The UV light source 300 may include at least one or more UV light modules, which may include one or more UV LEDs and a circuit board. In some exemplary embodiments, the UV light module may include a wavelength converter to covert wavelength of UV light emitted from the UV LED. The UV light modules may be mounted at various places inside the housing 200 to emit UV light towards one or more targets, such as the tray 500. While FIG. 1 exemplarily shows two UV light sources 300 mounted internally on upper portions of the housing 200, the inventive concepts are not limited to a particular number or locations of the UV light sources 300 in the housing 200. For example, when the housing 200 can accommodate more than two trays 500 therein, the UV light sources 300 may be formed at multiple locations in the housing 200 to effectively emit UV light towards each tray 500.

According to an exemplary embodiment, the UV light source 300 may include a first UV lighting unit and a second UV lighting unit to emit UV light having different wavelengths. For example, the first UV lighting unit may emit light in one among UV-A, UV-B, and UV-C range, and the second UV lighting unit may emit light in the other one among UV-A, UV-B, and UV-C range, without being limited thereto.

According to an exemplary embodiment, the UV apparatus 100 may include a lighting unit 700 to illuminate the interior of the housing 200. The lighting unit 700 may be disposed on a lower side of the housing 200 as shown in the drawings, but the inventive concepts are not limited to a particular location of the lighting unit 700 or numbers thereof. The lighting unit 700 may be implemented by a light emitting diode, without being limited thereto. In some exemplary embodiments, at least a first part of the lighting unit 700 may emit a first color light, such as a yellowish white, and a second part of the lighting unit 700 may emit a second color light, such as a bright white, such that whether the food or the container has been sterilized can additionally be visualized by the users. For example, the first part of the lighting unit 700 may emit light of the first color when the input door 410 is opened, and the second part of the lighting unit 700 may emit light of the second color when the output door 420 is opened. When the sterilization is in progress, the lighting unit 700 may not necessarily emit light. In this manner, the operator and the user may easily recognize whether the food and/or the container has been sterilized by the two different colors emitted from the lighting unit 700. While the first part of the lighting unit 700 has been exemplarily described as emitting a yellowish white light, and the second part of the lighting unit 700 has been exemplarily described as emitting a bright white light, the inventive concepts are not limited thereto as long as the two parts of the lighting unit 700 may emit light having different colors that can illuminate the interior of the housing 200.

The doors 400 may include at least one input door 410 and an output door 420 disposed at two different sides of the UV apparatus 100. According to an exemplary embodiment, the input door 410 and the output door 420 may be disposed at opposite sides of the housing 200 as shown in FIG. 1. For example, the input door 410 may be formed on a side of the housing 200 that faces an opposite direction of DR1, and the output door 450 may be formed on another side of the housing 200 that faces a direction of DR1. In this manner, the chef, for example, may place the tray 500 through the input door 410 for sterilization, and a user, such as the consumer or the server, may take the sterilized food or the container out from the housing 200 through the output door 450.

In this manner, a bodily contact to the sterilized food or the container may be substantially reduced. More particularly, since the consumer or the server uses the output door 420 that faces a different direction from the input door 410, the consumer or the server may take the sterilized food from the UV apparatus 100 without touching the input door 410 touched by the chef.

Figure 3:
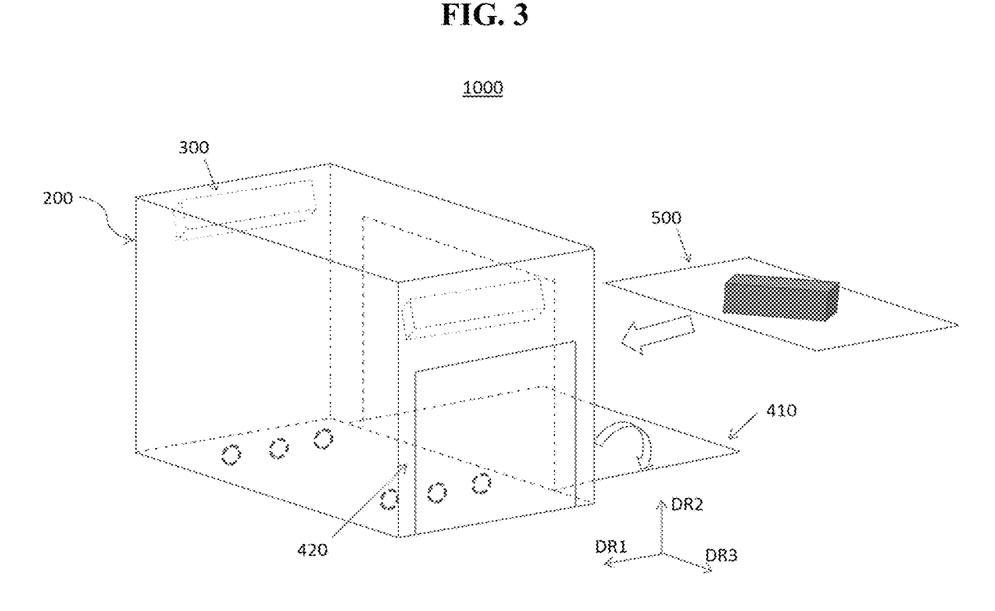
FIG. 3 is a schematic view of a UV apparatus according to an exemplary embodiment.

According to another exemplary embodiment, the input door 410 and the output door 420 may be disposed at adjacent sides of the housing 200, such as the one facing the direction of DR1 and the other facing a direction of DR3 as shown in FIG. 3. The UV apparatus 1000 shown in FIG. 3 is substantially the same as that shown in FIG. 1, except for the relative location of the input door 410 and the output door 420. As such, repeated descriptions of substantially the same elements will be omitted to avoid redundancy. According to still another exemplary embodiment, the input door 410 and the output door 420 may face the first direction of DR1 and a direction of DR2, respectively.

Figure 4:
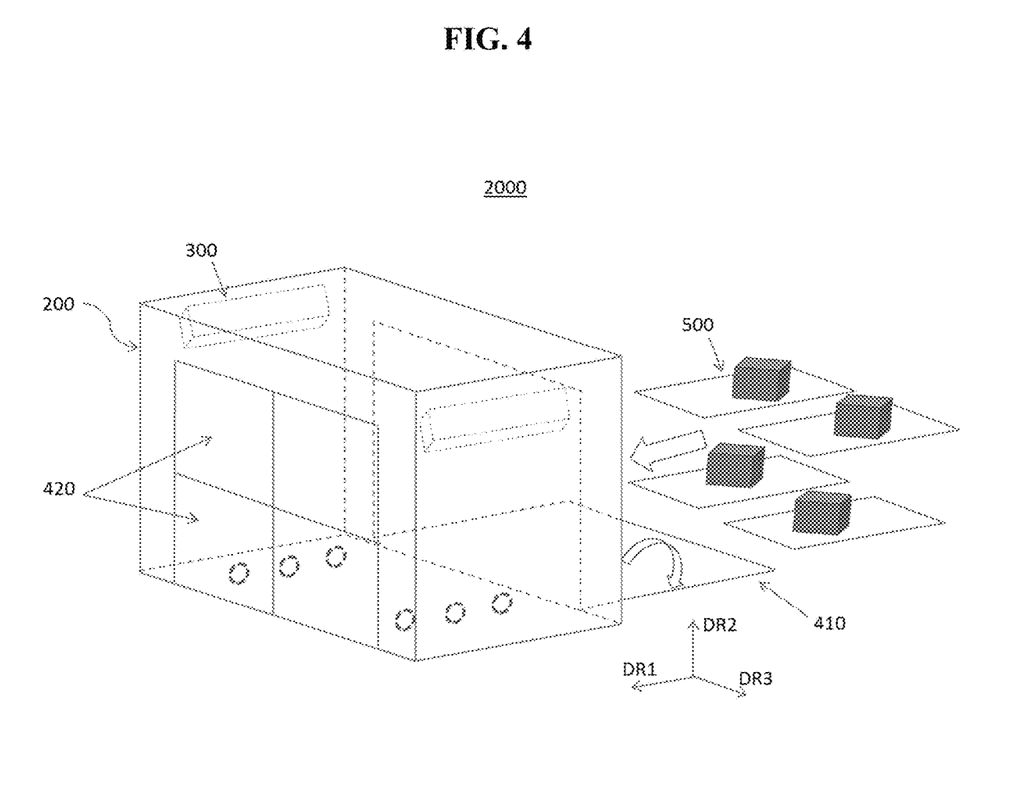
FIG. 4 is a schematic view of a UV apparatus according to an exemplary embodiment.

In some exemplary embodiments, at least one or more of the input door 410 and the output door 420 may be formed in plural, as long as the input door 410 and the output door 420 face different directions from each other, as shown in FIG. 4. In this case, each input door 410 and/or each output door 420 may provide an access to corresponding tray 500, such that a plural number of foods or containers may be sterilized simultaneously while minimizing bodily contact to the food. According to an exemplary embodiment, the size and the number of the input door 410 may be different from those of the output door 420. For example, the output door 420 may be formed in plural at one side of the housing 200, so that a user may access one or more of the output doors 420 that keep its food. In this case, the output door 420 may have a size less than that of the input door 410, without being limited thereto. The UV apparatus 2000 shown in FIG. 4 is substantially the same as that shown in FIG. 1, except for the relative size and the number of the input door 410 and the output door 420. As such, repeated descriptions of substantially the same elements will be omitted to avoid redundancy. As the input door 410 and the output door 420 according to an exemplary embodiment are formed on different sides of the housing 200, the UV apparatus 100 may be located in a boundary of the store between the chef and the user, such as near the cashier or in a pick-up location.

Referring back to FIG. 1, the UV apparatus 100 according to an exemplary embodiment may further include an access button, which may include a first access button 610 to operate the input door 410 and a second access button 620 to operate the output door. FIG. 1 exemplarily shows that the first and second access buttons 610 and 620 are disposed near the input and output doors 410 and 420, respectively, however, the inventive concepts are not limited thereto.

Figure 5:
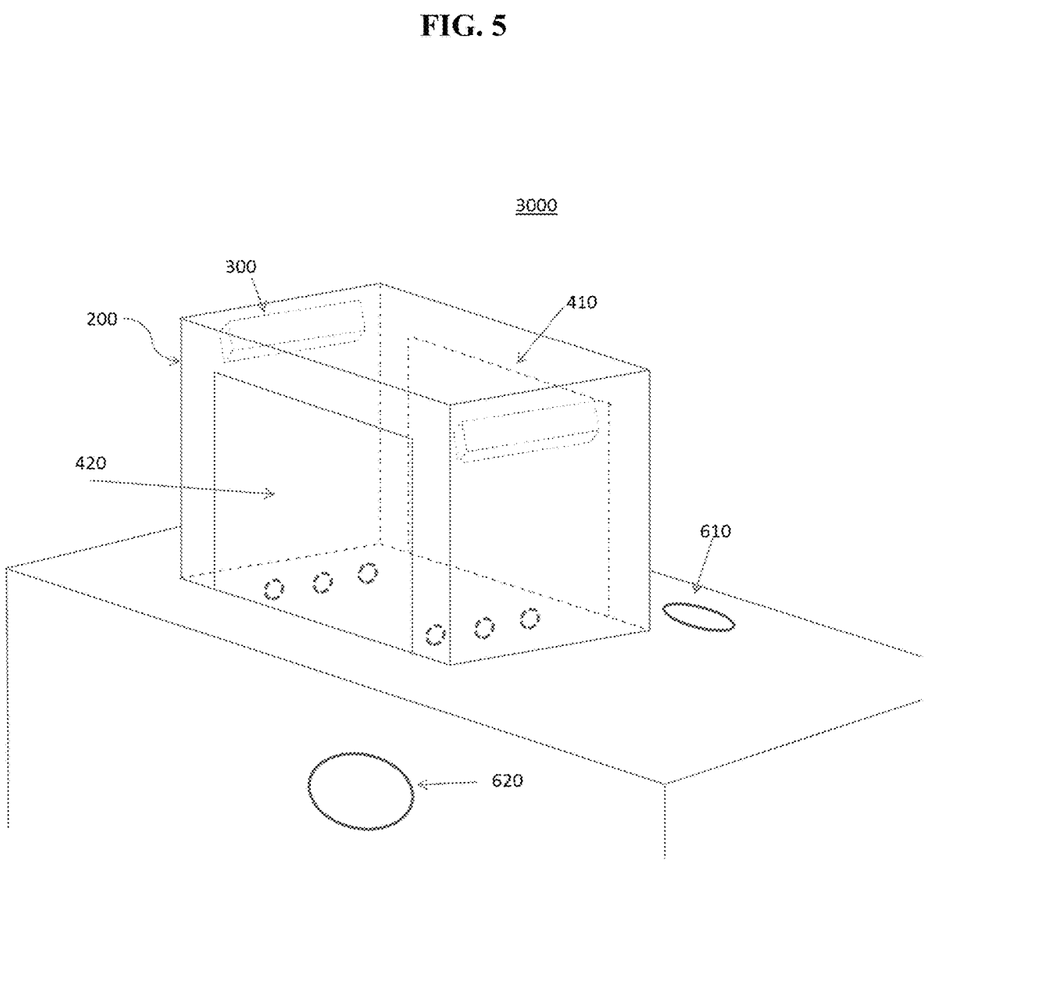
FIG. 5 is a schematic view of a UV apparatus according to an exemplary embodiment.

FIG. 5 is a schematic view of a UV apparatus 3000 according to an exemplary embodiment. The UV apparatus 3000 shown in FIG. 5 is substantially the same as that shown in FIG. 1, except for the relative location of the first and second access buttons 610 and 620. As such, repeated descriptions of substantially the same elements will be omitted to avoid redundancy.

Referring to FIG. 5, at least one of the first and second access buttons 610 and 620 may be placed remotely from the UV apparatus 3000, such as on the floor or between the floor and the UV apparatus 3000, so that the user may step on the access button or press the access button with a knee or an elbow to open the input door or the output door 410 and 420 and access the sterilized food without touching the UV apparatus 3000. In this case, the first and second access buttons 610 and 620 may be wired to the UV apparatus 3000 or wirelessly connected to the UV apparatus 3000. In some exemplary embodiments, the second access button 620 may be disposed at an elevation lower than the first access button 610 to avoid the risk of a user touching the second access button 620 with hand, which might have been contacted by a previous user.

In one exemplary implementation, once the sterilization is completed, the server may deliver the sterilized food or the container to the consumer through the output door 450 by using the tray 500 detachably placed in the housing 200, thereby avoiding direct contact to the sterilized food or container by the server. In another exemplary implementation, the consumer may directly take the sterilized food from the UV apparatus 3000 using the output door 420. In this case, when the UV apparatus 3000 includes the second access button 620 that allows access to the tray 500 without touching the output door 420, the consumer may directly take the food or the container from the UV apparatus 3000, which have not been touched by any other people after sterilization, even when the server and the consumer use the same output door 450.

In some exemplary implementations, the second access button 620 may be activated through a voice recognition system or through a mobile device, in order to avoid any bodily contact to the output door 450 or the second access button 620 itself. In this case, the second access button 620 may be omitted and a processor of the UV apparatus 100 may cause the output door 420 to open automatically upon receiving user's command once the sterilization has been completed. In some exemplary embodiments, an additional access button may be placed near the input door 410, to further avoid a bodily contact to the UV apparatus 100. When the output door 450 is formed in plural, the access button may also be formed in plural, respectively.

The processor may control the operation of the UV apparatus 100. For example, the processor may cause the locking unit 800 to lock the doors 410 and 420 while the UV light source 300 is turned on during the disinfecting process to prevent direct exposure of UV light to people. The locking unit 800 may be disposed on the doors 410 and 420 or in the housing 200, without being limited thereto. In some exemplary embodiments, the locking unit 800 may be formed in plural. In this manner, the processor according to an exemplary embodiment may sequentially operate the input door 410, the UV light source 300, and the output door 420.

The processor may control the duration of the sterilization process. According to an exemplary embodiment, the processor causes the UV light source 300 to emit UV light for about 30 seconds for sterilization. In general, extensive time for sterilization may deteriorate the quality of the food, such as taste, temperature, and moisture. In addition, overexposing the food to UV light for sterilization may damage nutrients in the food, such as proteins, fibers, and vitamins. As another example, a duration of sterilization process for less than about 30 seconds may reduce the likelihood of a user undesirably contacting other areas in the store which can be contaminated. As such, the processor according to an exemplary embodiment may cause the UV light source 300 to emit UV light for about 30 seconds or less for sterilization. In another exemplary embodiment, the processor may drive the UV light source 300 to emit UV light for about 10 to about 20 seconds at about 0.1 joules/cm$^2$ for sterilization to avoid the quality of the food and the container from being deteriorated.

According to an exemplary embodiment, the UV apparatus 100 may further include a first display near or in the input door 410, and a second display near or in the output door 420, each of which may indicate the operating status of the UV apparatus 100. The second display may provide the progress of the sterilization, information message about operating the output door 420 or the store, or entertainment contents to avoid the customer from undesirably touching the UV apparatus 100 or other areas of the store. The housing 200 may further include an input device near the input door 410, through which the chef may input an operation command of the UV apparatus 100, such as initiating the sterilization, an operation time, and so forth. In some exemplary embodiments, the input device may be included in the first display using a touch sensing function, for example. The UV apparatus 100 may also include a speaker to inform the status of the UV apparatus 100 to the user. For example, when a user activates the access button while the sterilization is in progress, the processor of the UV apparatus 100 may keep the doors 400 locked and inform the user the status of the UV apparatus, through the speaker, for example.

Figure 6:
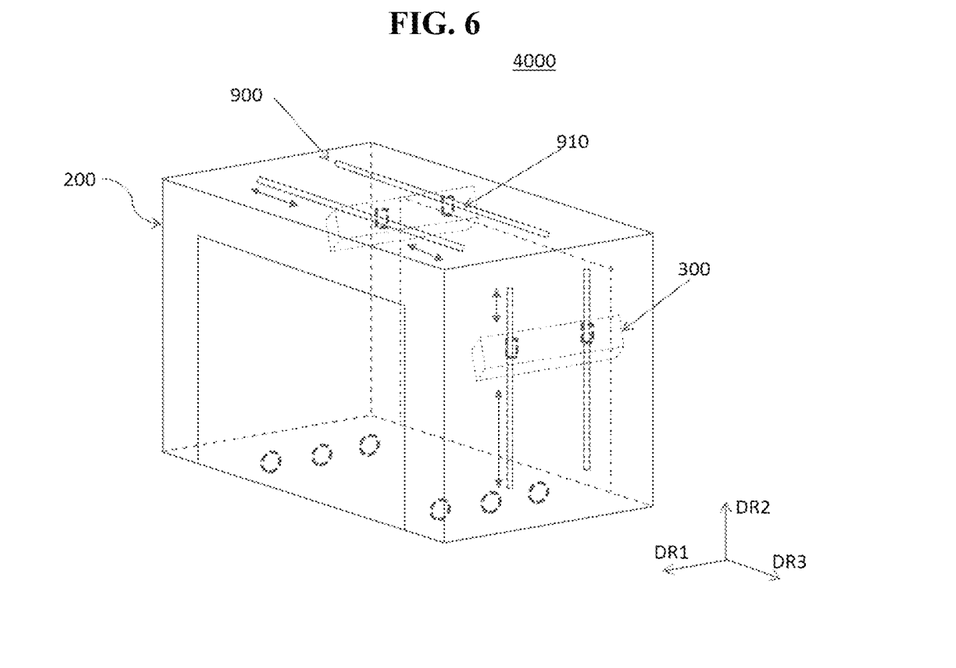
FIG. 6 is a schematic view of a UV apparatus according to an exemplary embodiment.

FIG. 6 is a schematic view of a UV apparatus 4000 according to an exemplary embodiment. The UV apparatus 4000 shown in FIG. 6 is substantially the same as that shown in FIG. 1, except for rails 900. As such, repeated descriptions of substantially the same elements will be omitted to avoid redundancy.

Referring to FIG. 6, the UV apparatus 4000 according to an exemplary embodiment may additionally include rails 900 inside the housing 200. The rails 900 may extend along at least one side of the housing 200. The rails 900 may provide a pathway through which UV light source 300 may slide along. In this case, the UV light source 300 may be coupled to at least one or more mount 910, which can be detachably coupled to the rail 900, to facilitate the movement of the UV light source 300 along the rail 900. In this manner, even when a number of food and/or the container are placed in the tray 500, UV light may be effectively emitted towards the foods and the containers for sterilization and disinfection. According to an exemplary embodiment, the rails 900 may be formed in sides of the housing on which the input and output doors 410 and 420 are not formed. Two or more rails 900 that extend in parallel may be formed as a group such that the UV light source 300 may be stably mounted on the rails 900 by the mounts 910. A plural groups of rails 900 may extend in directions that intersect each other, without being limited thereto.

Figure 7:
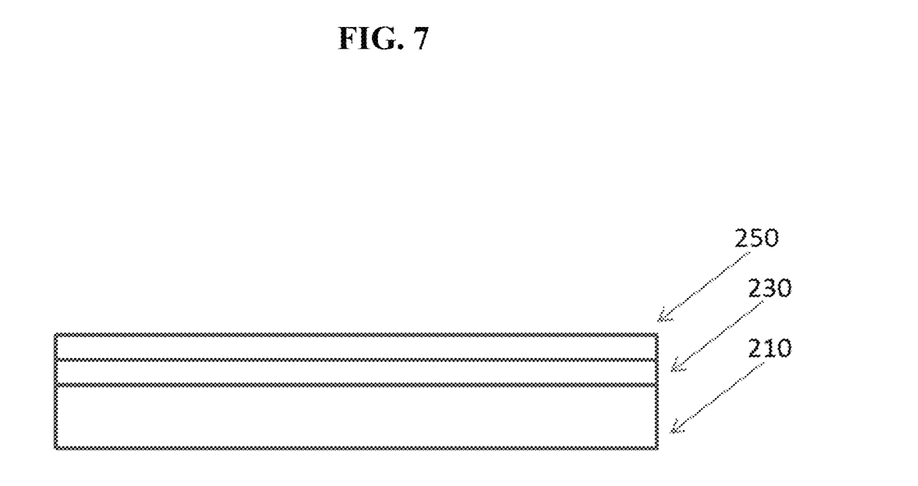
FIG. 7 is a schematic view of a side of the housing according to an exemplary embodiment.

FIG. 7 is a schematic cross-sectional view of one side of the housing according to an exemplary embodiment.

Referring to FIG. 7, the housing 200 according to an exemplary embodiment may include an inner wall 210, an insulation film 230, and a reflective film 250. The inner wall 210 may include metal or an inorganic material to provide an internal area of the housing 200. The insulation film 230 may be disposed on the inner wall 210 may maintain the temperature in the housing 200 and insulate the interior of the housing 200. The insulation film 230 may include inorganic material or an organic material without being limited thereto. The reflective film 250 may be disposed on the insulation film 230. The reflective film 250 may reflect UV light emitted from the UV light source 300 to increase sterilizing efficiency.

According to exemplary embodiment, a disinfecting apparatus may include a first door and a second door disposed on different sides of the housing to minimize the food and/or the container sterilized by the UV light source from being contacted by multiple people to prevent or at least suppress spread of disease by direct human contact.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A disinfecting apparatus comprising:
   a housing to accommodate at least one tray therein, the housing having a first side and a second side;
   an ultraviolet (UV) light source disposed in the housing and configured to emit UV light towards the tray;
   a lighting unit spaced apart from the UV light source and configured to emit white light; and
   a plurality of doors including a first door and a second door disposed on the first side and the second side of the housing, respectively,
   wherein the first door and the second door are configured to be opened in a direction away from the housing, and
   wherein the UV light source and the lighting unit are configured to emit light at different times.

2. The disinfecting apparatus of claim 1, wherein the first side and the second side are opposite to each other.

3. The disinfecting apparatus of claim 1, wherein:
   the housing further has a third side opposite to the first side; and
   the first side and the second side are adjacent to each other.

4. The disinfecting apparatus of claim 1, further comprising a first access button to open at least one of the first door and the second door.

5. The disinfecting apparatus of claim 4, wherein the first access button is disposed in the first side of the housing.

6. The disinfecting apparatus of claim 4, wherein the first access button is disposed remotely from the housing.

7. The disinfecting apparatus of claim 1, wherein both of the size and the number of the first door are different from that of the second door.

8. The disinfecting apparatus of claim 1, further comprising a processor to sequentially operate the first door, the UV light source, and the second door.

9. The disinfecting apparatus of claim 8, further comprising a locking unit disposed in the housing,
   wherein the processor causes the locking unit to keep the first and second doors from opening while the UV light source emits UV light.

10. The disinfecting apparatus of claim 8, wherein the UV light source is configured to emit light having a wavelength in a range of about 200 nm to about 280 nm at about 0.1 joules/cm$^2$.

11. The disinfecting apparatus of claim 10, wherein the UV light source is configured to emit UV light towards the tray less than about 30 seconds.

12. The disinfecting apparatus of claim 11, wherein the UV light source is configured to emit UV light towards the tray for about 10 to about 20 seconds.

13. The disinfecting apparatus of claim 1, wherein the tray is configured to extend outwardly from the housing via the second door once the UV light emission has been completed.

14. The disinfecting apparatus of claim 1, wherein the UV light source includes a first UV lighting unit and a second UV lighting unit configured to emit UV light having different wavelengths.

15. The disinfecting apparatus of claim 14, wherein the lighting unit is configured to illuminate the interior of the housing.

16. The disinfecting apparatus of claim 15, wherein the lighting unit is configured to emit light having a first color when the first door is opened, and is configured to emit light having a second color different from the first color when the second door is opened.

17. The disinfecting apparatus of claim 1, further comprising a reflective film disposed in the housing.

18. A disinfecting apparatus comprising:
a housing to accommodate at least one tray therein, the housing having a first side and a second side;
an ultraviolet (UV) light source disposed in the housing and configured to emit UV light towards the tray;
a plurality of doors including a first door and a second door disposed on the first side and the second side of the housing, respectively,
a first access button to open at least one of the first door and the second door; and
a second access button to open the other one of the first door and the second door,
wherein the first door and the second door are configured to be opened in a direction away from the housing.

19. The disinfecting apparatus of claim 18, wherein the second access button is disposed at a lower elevation that the of the first access button.

20. A disinfecting apparatus comprising:
a housing to accommodate at least one tray therein, the housing having a first side and a second side;
a plurality of doors including a first door and a second door disposed on the first side and the second side of the housing, respectively;
an ultraviolet (UV) light source disposed in the housing and configured to emit UV light towards the tray;
a rail disposed inside the housing; and
a mount on which the UV light source is disposed and coupled to the rail,
wherein the first door and the second door are configured to be opened in a direction away from the housing, and
wherein the mount is configured to slide along the rail within the housing while emitting UV light towards the tray.

* * * * *